United States Patent [19]

Holloway, Jr.

[11] 4,279,344
[45] Jul. 21, 1981

[54] HEAT-SEALABLE AND PEELABLE LAMINATED PACKAGING CONSTRUCTION

[75] Inventor: Fred W. Holloway, Jr., Richmond, Va.

[73] Assignee: Reynolds Metals Company, Richmond, Va.

[21] Appl. No.: 106,906

[22] Filed: Dec. 26, 1979

[51] Int. Cl.³ .................... B65D 75/30; B65D 75/32; B32B 27/08; B65D 17/00

[52] U.S. Cl. .................................. 206/631; 229/43; 229/62

[58] Field of Search ............... 206/631, 440, 439, 484; 229/43, 62

[56] References Cited

U.S. PATENT DOCUMENTS

| | | | |
|---|---|---|---|
| 2,954,116 | 9/1960 | Maso et al. | 206/631 |
| 3,204,760 | 9/1965 | Whiteford | 206/525 |
| 3,217,871 | 11/1965 | Lee | 206/440 |
| 3,326,450 | 6/1967 | Langdon | 229/62 |
| 3,454,210 | 7/1969 | Spiegel et al. | 229/43 |
| 3,582,427 | 1/1971 | Bacskai | 156/283 |
| 3,616,898 | 11/1971 | Massle | 206/216 |
| 3,625,348 | 12/1971 | Titchenal | 206/484 |
| 3,655,503 | 4/1972 | Stanley et al. | 206/631 |
| 3,665,302 | 2/1975 | Kane | 229/43 |
| 3,868,433 | 2/1975 | Bartz et al. | 260/876 R |
| 3,946,871 | 3/1976 | Strum | 229/43 |
| 3,988,499 | 10/1976 | Reynolds | 428/474 |
| 4,014,433 | 3/1977 | Cerwin | 206/63.3 |

FOREIGN PATENT DOCUMENTS

1171085  11/1969  United Kingdom .

*Primary Examiner*—William T. Dixson, Jr.
*Attorney, Agent, or Firm*—Glenn, Lyne, Girard & McDonald

[57] ABSTRACT

A peelable and heat-sealable packaging construction is disclosed. This packaging construction is formed from a pair of members, each member comprising a central structural barrier layer formed of a metallic foil, such as aluminum foil, paperboard or the like, an outer plastics resin covering layer for protection of the central structural barrier layer and an inner sealing layer formed from polypropylene or a polyethylene-polypropylene co-polymer, each blended with between about 15 to 35 percent by weight, and preferably between about 20 to 30 percent by weight, of an ionomer, such as Surlyn ® resin or ethylene methylacrylate. The sealing layers can be heat-sealed to one another to produce a bond which is able to withstand retort sterilization of the sealed packaging construction and which also forms a peelable seal. The packaging construction of the present invention is especially useful in packaging foodstuffs and medical supplies, such as sutures, surgical implements and the like, which must be readily accessible and sterile.

9 Claims, 1 Drawing Figure

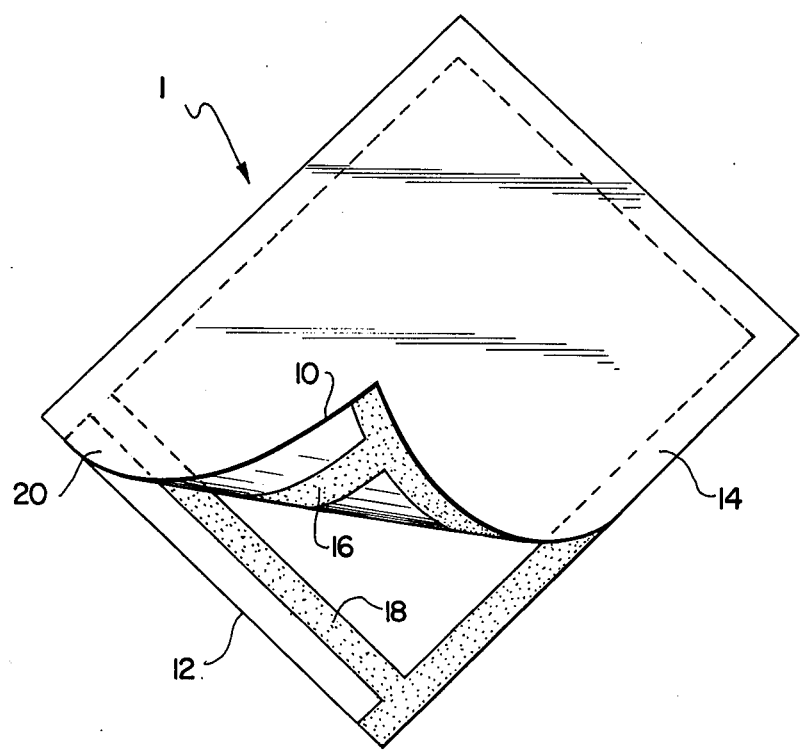

HEAT-SEALABLE AND PEELABLE LAMINATED PACKAGING CONSTRUCTION

BACKGROUND OF THE INVENTION

Heat-sealed laminated packaging structures are regularly employed to contain numerous materials. It is common for laminated bags to be used to contain surgical implements, including sutures, scalpels and the like. It is also becoming increasingly popular to employ heat-sealed laminated bag constructions as a replacement for cans in holding foodstuffs for extended periods of time.

A problem which is common to these different uses for laminated packaging structures is the sterilization of the materials contained within the constructions. Prior known laminated packaging constructions for foodstuffs provided a heat seal which was sufficiently strong to hold the foodstuffs contained therein, even under the conditions of retorting to sterilize the foodstuffs after packaging thereof, which retorting typically occurs at temperatures in the range of 250° F. (121° C.). However, such bonds typically have peel strengths in the range of about 14 to 18 pounds per inch (2500.4 to 3204.8 grams per centimeter), which is far too high to permit peeling of the seal by hand.

Peelable heat seals have been obtained in the packaging of medical supplies, such as sutures and the like. These heat seals have seal strengths of about 2 to 3 pounds per inch (357.2 to 535.8 grams per centimeter) as sealed. However, these seals cannot withstand the retort sterilzation process, resulting in failure of the seals. Since such containers cannot be effectively sterilized after sealing thereof, it is necessary that such medical supply material be sealed within their packages under sterile conditions, such as in the presence of a sterile gas.

It is desirable, therefore, to produce a laminated packaging construction which provides a heat seal having the ability to withstand retorting to enable sterilization of a package after sealing thereof and which is peelable by hand after retorting to enable opening of the package without resorting to external opening means, such as cutting apparatus.

THE PRESENT INVENTION

By means of the present invention, such a laminated packaging construction is provided. The laminated packaging construction of the present invention comprises a pair of members which are heat-sealed to one another. Each of the members comprises a central structural barrier layer, which may be formed of metallic foil, such as aluminum foil, paperboard and the like. Each of these central structural barrier layers has an outer plastics resin layer laminated thereto to protect the central structural barrier layer. Each of these central structural barrier layers also has laminated to its inner side, such as by extruding thereon, a plastics resin sealing layer, which sealing layer is formed of polypropylene or a polyethylene-polypropylene co-polymer, containing up to about 5 percent by weight polyethylene, blended with between about 15 and 35 percent by weight, and preferably between about 20 and 30 percent by weight, of an ionomer, such as Surlyn ® ionomer or ethylene methylacrylate. The bond formed when heat sealing the plastics resin sealing layers of these two members to form a packaging construction is hand peelable and at the same time is capable of withstanding retorting to sterilize the packaging construction and its contents.

BRIEF DESCRIPTION OF THE DRAWING

The laminated packaging construction of the present invention will be more fully described with reference to the drawing in which:

The FIGURE is an isometric view of a bag construction which has been formed according to the teachings of the present invention, with the heat seal thereof partially peeled.

DETAILED DESCRIPTION OF THE PREFERRED EMBODIMENTS

Turning now to the FIGURE, a laminated bag construction 1 is illustrated. The bag construction 1 comprises a pair of lamina 10 and 12. These lamina 10 and 12 are heat-sealed to one another by means commonly employed in the art, such as by the use of heated bars maintained at temperatures ranging between about 400° and 475° F. (204° and 246° C.) along a seal line 14. A region 20 at the top edge of the bag construction 1 is left unsealed. This region 20 is the region at which the two lamina 10 and 12 may be grasped by hand to peel the lamina 10 and 12 apart along the heat seal 14 and remove the contents from the bag construction 1. Regions 16 and 18 of lamina 10 and 12, respectively, illustrate peeled portions of the heat seal 14.

The lamina 10 and 12 are each formed from a plurality of layers. The outside of the bag construction 1, formed of the outer layers of the lamina 10 and 12, are formed of a plastics resin material, such as a polyester or polyamide resin. These outer plastic resin layers provide protection for central structural barrier layers. The central structural barrier layers may be formed of a metallic foil, such as aluminum foil, or paperboard. Preferably, the material forming this central structural barrier layer is aluminum foil, having a thickness ranging between about 0.0003 and 0.001 inches (0.0076 and 0.0254 centimeters). The outer plastics resin layers are laminated to the central structural barrier layers by means such as extrusion or adhesive bonding. Preferably, adhesive bonding, employing a thermosetting adhesive to withstand retorting, is used.

Each of these central structural barrier layers is laminated on its inner surface to a heat-sealable layer, which layers form the inside of the bag construction 1. It is these heat-sealable layers which provide the heat seal which is both retortable and peelable. The heat-sealable layers are plastics resin film layers and may be laminated onto the central structural barrier layers by adhesives, extrusion or the like. Preferably, the heat-sealable layers are extruded onto the central structural barrier layers. Optionally, and preferably, a primer layer, such as a modified polypropylene dispersion, is interposed between the central structural barrier layers and the plastics resin heat-sealable layers.

The heat-sealable layers are formed of a blend of plastics resins. A polypropylene or a polyethylene-polypropylene co-polymer, containing up to about 5 percent by weight polyethylene, is blended with an ionomer resin, such as Surlyn ® resin or an ethylene methylacrylate resin. The ionomer resin is present in an amount between about 15 and 35 percent by weight, and preferably between about 20 and 30 percent by weight. Below about 15 percent by weight ionomer, the heat seal becomes too strong to be peelable by hand after retorting. Above about 35 percent by weight ionomer, the heat seal becomes too weak to withstand retort sterilization, which typically takes place at temperatures in the range of 250° F. (121° C.). Between about 15 and 35 percent by weight ionomer, the heat seal 14 has a seal strength of between about 2.0 and 8.0 pounds per inch (357.2 and 1428.8 grams per centimeter), which is sufficient to withstand retort sterilization of the packaging construction and which can readily be peeled open by hand, based upon the nature of the specific packaging construction, as will be more fully described below.

The polypropylene employed in the formation of the heat-sealable layer preferably has a melt index of between about 4 and 10. When employed, the polyethylene has a melt index ranging between about 4 and 10.

The formation of the heat-sealable plastics resin layers can be accomplished according to the process described in British Pat. No. 1,171,085, the disclosure of which is incorporated herein by reference.

While the packaging construction of the present invention has thusfar been illustrated with reference to a bag construction, this is not the only packaging structure which may be formed of the retortable and peelable heat-sealed members. For example, one of the members could be preformed into a cup-like shape, with the second member being heat sealed onto the lip of the cup-like shape as a lid. The lid may include a portion thereof extending beyond the rim of the cup, to be used as a pull element for peeling. Such a packaging construction would have the same properties as the laminated bag structure previously described. Further, since the area of sealing is smaller than in a bag structure, the seal strengh may be higher than in the bag structure and still permit peeling by hand. For a cup lid, seal strenghs of up to about 8 pounds per inch (142.8 grams per centimeter) would be permissable, while for a bag structure as illustrated in the FIGURE peel strenghs only as high as about 3.0 pounds per inch would be employed.

EXAMPLES

Bag structures as illustrated in the FIGURE were produced. Each of these bag structures was formed from a pair of members, each member comprising an outer plastics resin layer formed of a 0.00048 inch (0.00122 centimeter) polyethylene terephthalate polyester film, an adhesive layer formed of 2 pounds per 3000 square foot (0.0033 grams per square meter) catalyzed polyurethane adhesive, a central structural barrier layer formed from 0.00035 inch (0.00089 centimeter) aluminum foil, a primer on the inner side of the aluminum foil formed from 1 pound per 3000 square feet (0.00017 grams per square meter) modified polypropylene dispersion and a heat-sealable plastics resin sealing layer formed from 0.003 inch (0.00076 centimeter) polypropylene blended with Surlyn ® resin in varying amounts, as in the chart below. The bags were sealed at various sealing temperatures, with a dwell time at the sealing temperature of 0.75 seconds and a sealing pressure of 40 pounds per square inch (0.28 kilograms per square meter) to give the following results:

| TEMP. °F. | TEMP. °C. | SURLYN ® resin (by weight) | | | | |
|---|---|---|---|---|---|---|
| | | 10% | 15% | 20% | 25% | 30% |
| | | pounds peel per inch | | | | |
| 250° | 121.1 | 0.0 | 0.0 | 0.0 | 0.0 | 0.0 |
| 300° | 148.9 | 0.5 | 0.5 | 0.9 | 0.5 | 0.5 |
| 350° | 176.7 | 1.0 | 1.2 | 1.5 | 0.9 | 0.9 |
| 400° | 204.4 | 3.0 | 5.2 | 6.0 | 1.2 | 1.5 |
| 450° | 232.2 | 15.0 | 7.7 | 6.0 | 1.5 | 1.7 |

After obtaining these results, additional samples formed from the same components were prepared at a seal temperature of 450° F. (232.2° C.), a dwell time of 0.75 seconds and 40 pounds per square inch (0.28 kilograms per square meter) pressure and retorted to give the following results:

| % By Weight SURLYN ® resin | Heat Seal Strength After Retort | |
|---|---|---|
| | lb/in | gm/cm |
| 10 | 14.0 | 2500.4 |
| 15 | 7.0 | 1250.2 |
| 20 | 7.1 | 1268.1 |
| 25 | 2.0 | 357.2 |
| 30 | 2.8 | 500.1 |

From the foregoing, it is clear that the present invention provides a packaging construction which can be sterilized by means of retorting and which provides a peelable seal.

While presently preferred embodiments of the invention have been illustrated and described, it will be understood that the invention may be otherwise variously embodied and practiced within the scope of the following claims.

I claim:
1. A packaging construction, said construction comprising a pair of members fixed to one another, each of said members comprising an outer plastics resin protective layer, a central structural barrier layer and an inner plastics resin sealing layer, said inner plastics resin sealing layers being capable of being heat-sealed to one another and peelable under hand pressure and said inner plastics resin sealing layers being capable of withstanding retorting without damage to said heat seal, said inner plastics resin sealing layers being formed from polypropylene or a polypropylene-polyethylene copolymer, including up to about 5 percent by weight polyethylene, blended with between about 15 and 35 percent by weight of an ionomer resin.

2. The packaging construction of claim 1 wherein one of said members is preformed into a cup-like shape and said other member is a lid for said cup-like member.

3. The packaging construction of claim 2 wherein said lid incudes a pull region extending beyond the rim of said cup-like member.

4. The packaging construction of claim 1 wherein said construction is a bag.

5. The packaging construction of claim 4 wherein said bag includes an unsealed edge region for peeling of said members.

6. The packaging construction of claim 1 wherein said outer plastics region protective layers are formed from a polyester or a polyamide.

7. The packaging construction of claim 1 wherein said central structural barrier layers are formed from aluminum foil.

8. The packaging construction of claim 1 wherein said ionomer resin is present in an amount between about 20 and 30 percent by weight.

9. The packaging construction of claim 1 wherein said ionomer resin is Surlyn ® or ethylene-methylacrylate.

* * * * *